United States Patent
Xu et al.

(10) Patent No.: US 7,371,880 B2
(45) Date of Patent: *May 13, 2008

(54) COPPER (I) COMPOUNDS USEFUL AS DEPOSITION PRECURSORS OF COPPER THIN FILMS

(75) Inventors: Chongying Xu, New Milford, CT (US); Alexander Borovik, West Hartford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/626,363

(22) Filed: Jan. 23, 2007

(65) Prior Publication Data

US 2007/0116876 A1    May 24, 2007

Related U.S. Application Data

(63) Continuation of application No. 11/149,045, filed on Jun. 9, 2005, now Pat. No. 7,241,912, which is a continuation of application No. 10/869,532, filed on Jun. 16, 2004, now Pat. No. 7,166,732.

(51) Int. Cl.
*C07F 1/08* (2006.01)
*C23C 16/00* (2006.01)

(52) U.S. Cl. .............. 556/110; 106/1.26; 427/255.28

(58) Field of Classification Search ........... 556/110; 427/255.28; 106/1.26
See application file for complete search history.

(56) References Cited

U.S. PATENT DOCUMENTS

| | | | |
|---|---|---|---|
| 2,839,421 | A | 6/1958 | Albisetti |
| 3,076,834 | A | 2/1963 | Norton |
| 3,288,829 | A | 11/1966 | Wilinson |
| 3,356,527 | A | 12/1967 | Moshler et al. |
| 3,437,516 | A | 4/1969 | Tamborski |
| 3,594,216 | A | 7/1971 | Charles et al. |
| 3,988,332 | A | 10/1976 | Schrock |
| 4,147,556 | A | 4/1979 | Donley |
| 4,281,037 | A | 7/1981 | Choung |
| 4,401,474 | A | 8/1983 | Donley |
| 4,510,222 | A | 4/1985 | Okunaka et al. |

(Continued)

FOREIGN PATENT DOCUMENTS

DE      3447635 A1      7/1985

(Continued)

OTHER PUBLICATIONS

Barker, James, et al., "The coordination chemistry of the amidine ligand", "Coord. Chem. Rev.", Jul. 1994, pp. 219-300, vol. 133.

(Continued)

*Primary Examiner*—Porfirio Nazario-Gonzalez
(74) *Attorney, Agent, or Firm*—Steven J. Hultquist; Intellectual Property / Technology Law; Maggie Chappuis

(57) ABSTRACT

Copper (I) amidinate precursors for forming copper thin films in the manufacture of semiconductor devices, and a method of depositing the copper (I) amidinate precursors on substrates using chemical vapor deposition or atomic layer deposition processes.

31 Claims, 3 Drawing Sheets

U.S. PATENT DOCUMENTS

| | | |
|---|---|---|
| 4,529,427 A | 7/1985 | French |
| 4,726,938 A | 2/1988 | Rollat et al. |
| 4,898,842 A | 2/1990 | David |
| 4,908,065 A | 3/1990 | Tanitsu et al. |
| 5,034,372 A | 7/1991 | Matsuno et al. |
| 5,085,731 A | 2/1992 | Norman et al. |
| 5,094,701 A | 3/1992 | Norma et al. |
| 5,096,737 A | 3/1992 | Baum et al. |
| 5,098,516 A | 3/1992 | Norman et al. |
| 5,110,622 A | 5/1992 | Hasegawa et al. |
| 5,120,703 A | 6/1992 | Snyder et al. |
| 5,144,049 A | 9/1992 | Norman et al. |
| 5,165,960 A | 11/1992 | Platts |
| 5,187,300 A | 2/1993 | Norman |
| 5,204,314 A | 4/1993 | Kirlin et al. |
| 5,220,044 A | 6/1993 | Baum et al. |
| 5,225,561 A | 7/1993 | Kirlin et al. |
| 5,280,012 A | 1/1994 | Kirlin et al. |
| 5,322,712 A | 6/1994 | Norman et al. |
| 5,362,328 A | 11/1994 | Gardiner et al. |
| 5,376,409 A | 12/1994 | Kaloyeros et al. |
| 5,412,129 A | 5/1995 | DiCarolis |
| 5,453,494 A | 9/1995 | Kirlin et al. |
| 5,536,323 A | 7/1996 | Kirlin et al. |
| 5,591,483 A | 1/1997 | Winter et al. |
| 5,668,054 A | 9/1997 | Sun et al. |
| 5,679,815 A | 10/1997 | Kirlin et al. |
| 5,688,054 A | 11/1997 | Rabe |
| 5,711,816 A | 1/1998 | Kirlin et al. |
| 5,744,192 A | 4/1998 | Nguyen et al. |
| 5,767,301 A | 6/1998 | Senzaki et al. |
| 5,817,367 A | 10/1998 | Chun et al. |
| 5,820,664 A | 10/1998 | Gardiner et al. |
| 5,840,897 A | 11/1998 | Kirlin et al. |
| 5,919,522 A | 7/1999 | Baum et al. |
| 5,932,363 A | 8/1999 | Hu et al. |
| 5,994,571 A | 11/1999 | Zhuang et al. |
| 6,015,917 A | 1/2000 | Bhandari et al. |
| 6,086,779 A | 7/2000 | Bishop et al. |
| 6,099,903 A | 8/2000 | Kaloyeros et al. |
| 6,102,993 A | 8/2000 | Bhandari et al. |
| 6,110,529 A | 8/2000 | Gardiner et al. |
| 6,153,519 A | 11/2000 | Jain et al. |
| 6,269,979 B1 | 8/2001 | Dumont |
| 6,337,148 B1 | 1/2002 | Xu et al. |
| 6,379,748 B1 | 4/2002 | Bhandari et al. |
| 6,417,369 B1 | 7/2002 | Xu et al. |
| 6,440,202 B1 | 8/2002 | Xu et al. |
| 6,593,484 B2 | 7/2003 | Yasuhara et al. |
| 6,639,080 B2 | 10/2003 | Xu et al. |
| 2004/0215030 A1 | 10/2004 | Norman |
| 2005/0042372 A1 | 2/2005 | Denk et al. |
| 2005/0281952 A1 | 12/2005 | Xu et al. |
| 2005/0283012 A1 | 12/2005 | Xu et al. |
| 2006/0102895 A1 | 5/2006 | Hendrix et al. |

FOREIGN PATENT DOCUMENTS

| | | |
|---|---|---|
| DE | 4039449 A1 | 6/1992 |
| EP | 0 852 229 A2 | 7/1998 |
| EP | 1 142 894 A2 | 10/2001 |
| GB | 976573 A | 11/1964 |
| JP | 08-176224 A | 7/1996 |
| JP | 8176224 A | 7/1996 |
| WO | 0168948 A1 | 9/2001 |
| WO | 2004046417 A2 | 6/2004 |
| WO | 2006009590 A1 | 1/2006 |

OTHER PUBLICATIONS

Cotton, F. A., et al., "Experimental and theoretical studies of the copper(I) and silver(I) dinuclear N,N'-di-p-tolylformamidinato complexes", "J. Am. Chem. Soc.", 1988, pp. 7077-7083, vol. 110, No. 21.

Dias, H.V. Rasika, et al., "Coinage metal complexes of 3,5-bis(trifluoromethyl)pyrazolate ligand Synthesis and characterization . . . ", "J. Fluor. Chem.", Apr. 24, 2000, pp. 163-169, vol. 103, No. 2.

Edelmann, Frank T., "N-silyated benzamidines: versatile building blocks in main group and coordination chemistry", "Coord. Chem. Rev.", Dec. 1994, pp. 403-481, vol. 137.

Kilner, Melvyn, et al., "Studies of Amidino-Complexes of Copper(I) and (II). Carboxylate Analogues", "Polyhedron", 1983, pp. 1379-1388, vol. 2, No. 12, Publisher: Pergamon Press Ltd., Published in: Great Britain.

Lim, Booyong S., et al., "Synthesis and Characterization of Volatile, Thermally Stable, Reactive Transition Metal Amidinates", "Inorg. Chem.", Dec. 1, 2003, pp. 7951-7958, vol. 42, No. 24.

Lim, Booyong S., et al., "Atomic layer deposition of transition metals", "Nature Materials", Nov. 2003, pp. 749-754, vol. 2, No. 11.

Shibayama, Koichi, et al., "Living Polymerization of Carbodiimides Initiated by Copper(I) and Copper(II) Amidinate Complexes ", "Macromolecules", Jun. 2, 1997, pp. 3159-3163, vol. 30, No. 11.

Van Vliet, P.I., et al., "Complexes of N,N'-substituted formamidines I. Compounds [M(RNC(H)NR')]n (M=CuI, AgI; R=p-TOLYL; R'=ALKYL; n=2,4)", "J. Organomet. Chem.", Oct. 9, 1979, pp. 89-100, vol. 179, No. 1.

Ainger, F.W., et al., Deposition of ferroelectric oxides by MOCVD, Prog. Crystal Growth and Charact., 1991, pp. 183-197, vol. 22.

Banaszak Holl, Mark M., et al., Ammonolysis of tantalum alkyls: Formation of cubic TaN and trimeric nitride, [Cp*MeTaN]3, Inorganic Chemistry, Apr. 18, 1990, pp. 1518-1526, vol. 29, No. 8.

Banaszak Holl, Mark M., et al., The ladder structure of [(tert-BuCH2)2TaN]5.cntdot.NH3.cntdot.2C7H8 and its relationship to cubic tantalum nitride, J. Amer. Chem. Soc., Oct. 24, 1990, pp. 7989-7994, vol. 112, No. 22.

Banaszak Holl, Mark M., et al., Conversion of [(tBuCH2)2TaN]5 to Cubic TaN: Related Syntheses, EHMO Calculations, and MAS and Spin Echo 15N NMR Spectros, Chem. Mater., Oct. 1996, pp. 2468-2480, vol. 8, No. 10.

Blanquet, E., et al., Evaluation of LPCVD Me-Si-N (Me=Ta, Ti, W, Re) diffusion barriers for Cu metallizations, Microelectronic Engineering, Nov. 1997, pp. 189-195, vol. 37/38.

Bogert, L. Jean, Chapter XVII, General classification of organic compounds, Fundamentals of Chemistry, 1924, pp. 184-187, Publisher: WB Saunders, Published In: Philadelphia.

Bradley, Donald C., et al., Metallo-organic compounds containing metal-nitrogent bonds: Part I, some dialkyamino derivatives of titanium and . . . , J. Chem. Soc., Oct. 1960, pp. 3857-3861.

Bradley, D.C., et al., Nuclear magnetic resonance studies on niobium and tantalum penta-alkoxides, J. Chem. Soc. (A), 1968, pp. 219-223.

Bradley, Donald C., et al., Transition-metal dialkylamides and disilylamides, Accounts of Chemical Research, 1976, pp. 273-280, vol. 9.

Buerger, Hans, et al., Titanium-nitrogen compounds. 9. Tris(dialkylamino)titanium derivatives of phosphorus and arsenic, CA: 72:132915, abstract of Inorganic and Nuclear Chemistry Letters, 1970, pp. 299-304, vol. 6, No. 3.

Catania, Phillip, et al., Low resistivity body-centered cubic tantalum thinl films as diffusion barriers between copper and silicon, J. Vac. Sci. Tech. A, 1992, pp. 3318-3321, vol. A10.

Chao, Yuan-Wei, et al., Preparation and properties of tantalum imido complexes and their reactions with alkynes. Coordination control through . . . , Inorganic Chemistry, Oct. 4, 1989, pp. 3860-3868, vol. 26, No. 20.

Chao, Yuan-Wei, et al., Preparation and properties of amido halide complexes of niobium and tantalum and their reactions with alkynes, Polyhedron, 1990, pp. 2709-2716, vol. 9, No. 22.

Chisholm, Malcom H., et al., Chloro(dimethylamido) compounds of tantalum(V): Preparation, properties, and structures of [Ta(NMe2)3Cl2]2, . . . , Inorganic Chemistry, Jun. 1, 1981, pp. 1859-1865, vol. 20, No. 6.

Chiu, Hsin-Tien, et al., Effect of hydrogen on deposition of tantalum nitride thin films from ethylimidotantalum complex, J. of Mater. Sci. Lett., Jan. 1992, pp. 570-572, vol. 11, No. 9.

Chiu, Hsin-Tien, et al., Tungsten nitride thin films prepared by MOCVD, J. Mater. Res., Jun. 1993, pp. 1353-1360, vol. 8, No. 6.

Cummins, Christopher C., et al., Synthesis of Terminal Vanadium(V) Imido, Oxo, Sulfido, Selenido, and Tellurido Complexes by Imido Group or Chalcogenide, Inorganic Chemistry, Mar. 30, 1994, pp. 1448-1457, vol. 33, No. 7.

Deutscher, R.L., et al., Eight coordinate tetrakis-chelate complexes of niobium(IV) and tantalum(IV), Inorganica Chimica Acta, 1970, pp. 645-650, vol. 4, No. 4.

Finn, A.A., et al., Chemical vapor deposition of platinum, palladium and nickel, The Chemistry of Metal CVD, 1994, Publisher: T.T. Kodas, M.J. Hampden-Smith, eds. A Diligent Effort was Made To Locate a Copy of This Reference, Including Contacting the British Library, Without Success. This Reference was Cited in U.S. Pat. No. 6,015,917, and the Examiner is Directed to the File History to Obtain a Copy of Same.

Fix, Renaud, et al., Chemical vapor deposition of vanadium, niobium, and tantalum nitride thin films, Chem. Mater., May 1993, pp. 614-619, vol. 5, No. 5.

Fuggle, J.C., et al., Reactions of Niobium and Tantalum Pentaflourides with Trimethylsilyldiethylamine and with Trimethylsilyl Chloride, J. Chem. Soc. Dalton Trans., 1972, pp. 1766-1768.

Gilman, Norman W., et al., Extension of the Smiles rearrangement. Displacement of an aromatic amide group by an amine nitrogen, J. Org. Chem., Jan. 26, 1973, pp. 373-377, vol. 38, No. 2.

Hieber, K., Structural and electrical properties of Ta and Ta nitrides deposited by chemical vapour deposition, Thin Solid Films, Nov. 1974, pp. 157-164, vol. 24, No. 1.

Hiskes, R., et al., Single source metalorganic chemical vapor deposition of low microwave surface resistance YBa2Cu3O7, Applied Physics Letters, Jul. 29, 1991, pp. 606-607, vol. 59, No. 5.

Holloway, Karen, et al., Tantalum as a diffusion barrier between copper and silicon: Failure mechanism and effect of nitrogen additions, Journal of Applied Physics, Jun. 1, 1992, pp. 5433-5444, vol. 71, No. 11.

Jacini, Giovanni, Organic derivatives of titanium, CA: 49:19704, abstract of Olii Minerali, Grassi e Saponi, Corori e Vernici, 1953, pp. 193-194, vol. 30.

Jiang, Qian, et al., Synthesis of mono- and bis(silyl) complexes of tantalum, Organometallics, Oct. 1991, pp. 3648-3655, vol. 10, No. 10.

Kapoor, P.N. et al., Organic compounds of niobium and tantalum IV. Reactions of niobium and tantalum pentaethoxides with β-diketones, Journal of the Less-Common Metals, May 1965, pp. 339-346, vol. 8, No. 5.

Kee, Terence P., Tantalum, Coordination Chemistry Reivews, Jan. 1995, pp. 181-194, vol. 138.

Kolawa, E., et al., Tantalum-based diffusion barriers in Si/Cu VLSI metallizations, Journal of Applied Physics, Aug. 1, 1991, pp. 1369-1373, vol. 70, No. 3.

Lappert, M.F. et al., Metal and Metalloid Amides, pp. 470-543, Publisher: John Wiley and Sons, A Diligent Effort was Made to Locate a Copy of This Reference, Including Contacting the British Library, Without Success. This Reference was Cited in U.S. Pat. No. 6,015,917, and the Examiner is Directed to the File History to Obtain a Copy of Same.

Li, Jian, et al., Copper-based metallization in ULSI structures, MRS Bulletin, Aug. 1994, pp. 15-18, vol. XIX, No. 8.

Li, Wentao, et al., Additives for stabilizing LiPF6-based electrolyes against thermal decomposition, J. Electrochem. Soc., 2005, pp. A1361-A1365, vol. 152, No. 7.

McLain, S.J., et al., Multiple metal-carbon bonds. 6. The reaction of niobium and tantalum neopentylidene complexes with simple olefins: . . . , J. Amer. Chem. Soc., May 11, 1977, pp. 3519-3520, vol. 99, No. 10.

Murarka, S.P., et al., Advanced multilayer metallization schemes with copper as interconnection metal, Thin Solid Films, Dec. 15, 1993, pp. 257-266, vol. 236, No. 1-2.

Narula, A.K., et al., Preparation and characterization of nobium (V) beta-diketonates, Synth. React. Inorg. Met. Org. Chem., 1983, pp. 1-19, vol. 13, No. 1.

Narula, A.K., et al., Preparation and Characterization of Tantalum(V) beta-Diketonates (Part II), Synth. React. Inorg. Met.-Org. Chem., 1983, pp. 887-898, vol. 13, No. 7.

Adherent and stable metallization of CVD diamond, Nasa Tech Briefs, Jun. 1997, pp. 63-64.

Diffusion barriers for GaAs and InP devices, Nasa Tech Briefs, Jun. 1997, p. 42.

Nugent, William A., et al., Structure and reactivity in the group %b t-butylimido complexes (Me2N)3_NBut; X-ray crystal and molecular structure of . . . , JCS Chem. Comm., 1978, pp. 579-580.

Nugent, William A., Synthesis of some d0 organoimido complexes of the early transition metals, Inorg. Chem., Mar. 16, 1983, pp. 965-969, vol. 22, No. 6.

Oakley, Sarah H., et al., Structural consequences of the prohibition of hydrogen bonding in copper-guanidine systems, Inorg. Chem., 2004, pp. 5168-5172, vol. 43, No. 16.

Olowolafe, J.O., et al., Interdiffusions in Cu/reactive-ion-sputtered TiN, Cu/chemical-vapor-deposited TiN, Cu/TaN, and TaN/Cu/TaN thin-film . . . , Journal of Applied Physics, Nov. 1, 1992, pp. 4099-4103, vol. 72, No. 9.

Ovchinnikov, Yu. E., et al., The crystal structures of the titanium-containing organosilicon compounds (SiMe3)3 and (SiMe3)3GeTi(Nme2)3, Metalloorg. Khim, (Organometallic Chem. In USSR), 1992, pp. 564-567, vol. 5, No. 5.

Ovchinnikov, Yu E., et al., Crystal and molecular structure of organosilicon derivatives of titanium (IV) (Me3Si)3SiTi(NEt2)3, and ClTi[N(SiMe3)2]3, CA: 125:100729, abstract of Izvestiya Akademii Nauk, Seriya Khimicheskaya, 1993, pp. 1473-1476, vol. 8.

Papadopoulos, E.P., Reaction of o-amononitriles with isocyanates. 2. A facile synthesis of imidazo[1,2-c]quinazoline-2,5-(3H,6H)dione, J. Heterocyclic Chem., May 1981, pp. 515-518, vol. 18.

Phule, Pradeep P., Sol-gel sythesis of ferroelectric lithium tantalate ceramics: FTIR investigation of the molecular modification of . . . , J. Mater. Res., Feb. 1993, pp. 334-338, vol. 8, No. 2.

Prostasiewicz, John D., et al., Synthesis and structural characterization of low-valent Group V phosphine complexes, Inorganic Chemistry, Sep. 30, 1992, pp. 4134-4142, vol. 31, No. 20.

Rossnagel, S.M., et al., Thin, high atomic weight refractory film deposition for diffusion barrier, adhesion layer, and seed layer applications, J. Vac. Sci. Technol. B, May 1996, pp. 1819-1827, vol. 14, No. 3.

Schrock, Richard R., et al., Multiple Metal-Carbon Bonds. 8. a Preparation, Characterization, and Mechanism of Formation of the Tantalum and . . . , J. Amer. Chem. Soc., May 24, 1978, pp. 3359-3370, vol. 100, No. 11.

Schrock, Richard R., Alkylidene complexes of niobium and tantalum, Accounts of Chemical Research, Mar. 1979, pp. 98-104, vol. 12, No. 3.

Simmonds, M.G, et al., Chemical vapor deposition of aluminum, The Chemistry of Metal CVD, Kodas, T. and Hampden-Smith, M. (eds), 1994, pp. 48-103, Publisher: VCH Publishers, Published in: New York.

Small, M.B., et al., On-chip wiring for VLSI: Status and directions, IBM J. Res. Dev., Nov. 1990, pp. 858-867, vol. 34, No. 6.

Stolz, M., et al., Universal chemical vapour deposition system for metallurgical coatings, Thin Solid Films, Feb. 18, 1983, pp. 209-218, vol. 100, No. 3.

Sugiyama, Kozoh, et al., Low temperature deposition of metal nitrides by thermal decomposition of organometallic compounds, J. Electrochem. Soc., Nov. 1975, pp. 1545-1549, vol. 122, No. 11.

Sun, S.C., et al., Diffusion barrier properties of CVD tantalum nitride for aluminum and copper interconnections, VMIC Conference, ISMIC, Jun. 27-29, 1995, pp. 157-161.

Suzuki, Toshiya, et al., Comparison of CVD TiN, PECVD WNx, and CVD W-Si-N as upper electrode materials for Ta2O5 DRAM capacitors, Advanced Metallization Conference, Sep. 28, 1997, Published in: San Diego.

Tilley, T. Don, The Reactivity of Transition Metal-Silicon Compounds, Final Technical Report, AD No. A200371, Aug. 8, 1988, Publisher: Defense Technical Information Center.

Tilley, T. Don., Transition-metal silyl derivatives, The Chemistry of Organic Silicon Compounds, Patai, Saul and Rappaport, Zvi (eds), 1989, pp. 1415-1477, Publisher: John Wiley & Sons, Published in: New York.

Tsai, M.H., et al., Metalorganic chemical vapor deposition of tantalum nitride by tertbutylimidotris(diethylamido)tantalum for advanced . . . , Appl. Phys. Lett., Aug. 21, 1995, pp. 1128-1130, vol. 67, No. 8.

Tsai, M.H., et al., Metal-organic chemical vapor deposition of tantalum nitride barrier layers for ULSI applications, Thin Solid Films, Dec. 1, 1995, pp. 531-536, vol. 270, No. 1-2.

Turner, Howard W., et al., Tantalum complexes containing diimido bridging dinitrogen ligands, J. Amer. Chem. Soc., Dec. 17, 1980, pp. 7809-7811, vol. 102, No. 26.

Ugolini, D., et al., Photoelectron spectroscopy studies of chemical vapor deposition of Ta from a TaF5 precursor on Si and SiO2 substrates, Journal of Applied Physics, Oct. 1, 1991, pp. 3899-3906, vol. 70, No. 7.

Van Buskirk, Peter C., et al., MOCVD growth of BaTiO3 in an 8-inch single-wafer CVD reactor, Proc. ISAF, Eighth Int'l Symp. Appl. Ferroelectrics, Aug. 31-Sep. 2, 1992, vol. 92.

Wang, Shi-Qing, et al., Step coverage comparison of Ti/TiN deposited by collimated and uncollimated physical vapor deposition techniques, J. Vac. Sci. Technol. B, May 1996, pp. 1846-1852, vol. 14, No. 3.

Wang, Shi-Qing, Barriers against copper diffusion into silicon and drift through silicon dioxide, MRS Bulletin, Aug. 1994, pp. 30-40.

Wang, Shi-Qing, et al., Film property comparison of Ti/TiN deposited by collimated and uncollimated physical vapor deposition techniques, J. Vac. Sci Technol. B, May/Jun. 1996, pp. 1837-1845, vol. 14, No. 3.

Werner, Robert P.M., et al., Tetracarbonylcyclopentadienyl Compounds of the Group V Transition Metals, Inorganic Chemistry, Feb. 1964, pp. 298-300, vol. 3, No. 2.

Williams, David N., et al., Half-sandwich imido complexes of niobium and tantalum, J. Chem. Soc. Dalton Trans., 1992, pp. 739-751.

Winter, Charles H., The chemical vapor deposition of metal nitride films using modern metalorganic precursors, Aldrichchimica Acta, 2000, pp. 3-12, vol. 33, No. 1.

Xue, Z., et al., Early-Transition-Metal Silyl Complexes Free from Anionic r-Ligands. A New Family of Alkyl, Alkylidene, and Alkylidyne . . . , J. Amer. Chem. Soc., Mar. 9, 1994, pp. 2169-2170, vol. 116, No. 5.

Zhang, Jiming, et al., Single liquid source plasma-enhanced metalorganic chemical vapor deposition of high quality YBa2Cu3O7-x thin films, Applied Physics Letters, Dec. 14, 1992, pp. 2884-2886, vol. 61, No. 24.

Zhang, Jiming, et al., Plasma enhanced metalorganic chemical vapor deposition of conductive oxide electrodes for ferroelectric BaTiO3 capacitor, Mater. Res. Soc. Symp. Proc., 1993, pp. 249-254, vol. 310.

Zhang, Jiming, et al., Metal organic chemical vapor deposition of LaSrCoO electrodes for ferroelectric capacitors, 6th ISAF Mtg., Mar. 1994.

Zinn, Alfred A., et al., Chemical vapor deposition of platinum, palladium and nickel, The Chemistry of Metal CVD, Kodas, T. and Hampden-Smith, M. (ed.), 1994, pp. 330-339, Publisher: VCH Publishers, Published in: New York.

Awaya, Nobuyoshi, et al., Deposition mechanism of copper CVD, Conference Proceedings ULSI-VH, 1992, pp. 345-354, Publisher: Materials Research Society.

Bohr, Mark T., Scaling of high performance interconnects, Conference Proceedings ULSI XII, 1997, pp. 3-10, Publisher: Materials Research Society.

Chi, K. M., et al., Synthesis and characterization of (beta-diketonato)copper(I)alkyne complexes: structural characterization of . . . , Inorganic Chemistry, Nov. 13, 1991, pp. 4293-4294, vol. 30, No. 23, Publisher: American Chemical Society.

Girolami, Gregory S., et al., Chemical vapor deposition of copper and copper oxide thin films for copper(l) tert-butoxide, Chemistry of Materials, 1989, pp. 8-10, vol. 1.

Houle, F. A., et al., Laser chemical vapor deposition of copper, Appl. Phys. Lett., 1985, pp. 204-206, vol. 46.

Jain, A., et al., Chemical vapor deposition of copper via disproportionation of hexafluoroacetylacetonato(1,5-cyclooctadiene)copper(I) . . . , Journal of Materials Research, Feb. 1992, pp. 261-264, vol. 7, No. 2, Publisher: Materials Research Society.

Kaloyeros, Alain E., et al., Low-temperature metal-organic chemical vapor deposition (LTMOCVD) of device-quality copper films for microelectronic . . . , Journal of Electronic Materials, Mar. 1990, pp. 271-276, vol. 19, No. 3, Publisher: The Minerals, Metals & Materials Society and the Institute of Electrical and Electronics Engineers.

Norman, J. A. T., et al., New OMCVD precursors for selective copper metallization, Journal de Physique IV, Colloque C2, Suppl. Au Journal de Physique II, Sep. 1991, pp. 271-278, vol. 1.

Oehr, C., et al., Thin copper films by plasma CVD using copper-hexafluoro-acetylacetonate, Applied Physics A: Solids and Surfaces, Feb. 1988, pp. 151-154, vol. 45, No. 2.

Reisman, A., et al., Chemical vapor deposition of copper from copper (II) hexafluoroacetylacetonate, J. Electrochemical Soc., Nov. 1989, pp. 3525-3529, vol. 139, No. 11.

Shin, H. K., et al., Chemistry of Copper(I) beta-diketonate complexes. 2. synthesis, characterization, and physical properties of . . . , Inorganic Chemistry, Feb. 5, 1992, pp. 424-431, vol. 31, No. 3, Publisher: American Chemical Society.

Shin, H.K., et al., MOCVD of Titanium Nitride from a New Precursor, Ti[N(CH3)C2H5]4 , Chem. Mater., Jan. 1997, pp. 76-80, vol. 9, No. 1.

Van Hermert, R. L., et al., Vapor deposition of metals by hydrogen reduction of metal chelates, J. Electrochemical Soc., 1965, pp. 1123-1126, vol. 112, No. 11.

COPPER (I) COMPOUNDS USEFUL AS DEPOSITION PRECURSORS OF COPPER THIN FILMS

CROSS REFERENCE TO RELATED APPLICATIONS

This is a continuation of U.S. patent application Ser. No. 11/149,045 for "Copper (I) Compounds Useful as Deposition Precursors of Copper Thin Films" filed on Jun. 9, 2005 now U.S. Pat. No. 7,241,912 in the name of Chongying Xu, et al., which in turn is a continuation of U.S. patent application Ser. No. 10/869,532 for "Copper (I) Compounds Useful as Deposition Precursors of Copper Thin Films" filed on Jun. 16, 2004 in the name of Chongying Xu, et al., and issued Jan. 23, 2007 as U.S. Pat. No. 7,166,732.

FIELD OF THE INVENTION

The present invention relates generally to novel copper (I) amidinates and their synthesis, and to a method for production of copper circuits in microelectronic device structures using the novel copper precursors.

DESCRIPTION OF THE RELATED ART

As a result of its low resistivity, low contact resistance, and ability to enhance device performance through the reduction of RC time delays, copper has emerged as a preferred metal for metallization of very large scale integrated (VLSI) devices. Copper metallization has been adopted by many semiconductor device manufacturers for production of microelectronic chips, thin-film recording heads and packaging components.

Chemical vapor deposition (CVD) of copper provides uniform coverage for the metallization. Atomic layer deposition (ALD), which is a modified CVD process, also provides uniform coverage which is critical for copper seed layers. Liquid CVD precursors and/or solid precursors dissolved into solvents enable direct injection and/or the liquid delivery of precursors into a CVD or ALD vaporizer unit. The accurate and precise delivery rate can be obtained through volumetric metering to achieve reproducibility during CVD or ALD metallization of a VLSI device.

Many fluorine and/or oxygen-containing copper CVD precursors are commercially available, including (hfac)Cu(MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and VTMS=vinyltrimethylsilane.

Copper metallization in integrated circuit manufacture typically utilizes a barrier layer between the copper layer and the underlying structure in order to prevent detrimental effects that may be caused by the interaction of a copper layer with other portions of the integrated circuit. A wide range of barrier materials is conventionally utilized, including materials comprising metals, metal nitrides, metal silicides, and metal silicon nitrides. Exemplary barrier materials include titanium nitride, titanium silicide, tantalum nitride, tantalum silicide, tantalum silicon nitrides, niobium nitrides, niobium silicon nitrides, tungsten nitride, and tungsten silicide. In instances where (hfac)CuL type precursors are used for copper metallization, interfacial layers are formed between the barrier layer and the copper layer, which cause the metallization to have poor adhesion and high contact resistivity.

The deficiencies of inferior adhesion and excessively high contact resistivity incident to formation of oxygen- and/or fluorine-containing interfacial layers when using (hfac)CuL copper precursors has been attributed to the hfac ligand, which contains both oxygen and fluorine. To overcome such deficiencies, it would be a significant advance in the art to provide copper precursors having a reduced oxy/fluoro content. It would be particularly advantageous to provide copper precursors of an oxygen-free character.

It is accordingly an object of the present invention to provide new anoxic (oxygen-free and fluorine-free) copper precursors and formulations, as well as methods of forming copper in the manufacturing of integrated circuits and other microelectronic device structures using such precursors and formulations.

SUMMARY OF THE INVENTION

The present invention relates generally to copper (I) amidinate compounds, which are advantageously of an oxygen-free and fluorine-free character, useful as source reagents for forming copper on substrates with improved adhesion, and to methods of using such copper (I) amidinate compounds.

The present invention in one aspect relates to a copper precursor compound of the formula:

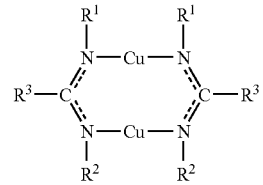

wherein:
$R^1$ and $R^2$ may be the same as or different from one another and each is independently selected from the group consisting of H, $C_1$-$C_6$ alkyl, $C_3$-$C_7$ cycloalkyl, aryl, and hydrocarbyl derivatives of silyl groups (e.g., —$SiR_3$, wherein R is independently selected from the group consisting of $C_1$-$C_6$ alkyl);
$R^3$ is selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups;

with the proviso that when $R^1$ and $R^2$ are isopropyl groups, $R^3$ is not a methyl group.

In another aspect, the present invention relates to a copper precursor formulation, comprising:
(a) a copper precursor compound of the formula:

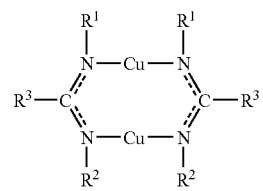

wherein:

$R^1$ and $R^2$ may be the same as or different from one another and each is independently selected from the group consisting of H, $C_1$-$C_6$ alkyl, $C_3$-$C_7$ cycloalkyl, aryl, and hydrocarbyl derivatives of silyl groups;

$R^3$ is selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups;

(b) a solvent composition for the precursor compound.

In yet another aspect, the present invention relates to a method of depositing copper on a substrate, comprising volatilizing a copper precursor of the formula:

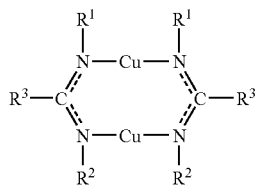

wherein:

$R^1$ and $R^2$ may be the same as or different from one another and each is independently selected from the group consisting of H, $C_1$-$C_6$ alkyl, $C_3$-$C_7$ cycloalkyl, aryl, and hydrocarbyl derivatives of silyl groups;

$R^3$ is selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups;

with the proviso that when $R^1$ and $R^2$ are isopropyl groups, $R^3$ is not a methyl group, to form a precursor vapor and contacting the precursor vapor with the substrate under elevated temperature vapor decomposition conditions to deposit copper on the substrate.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
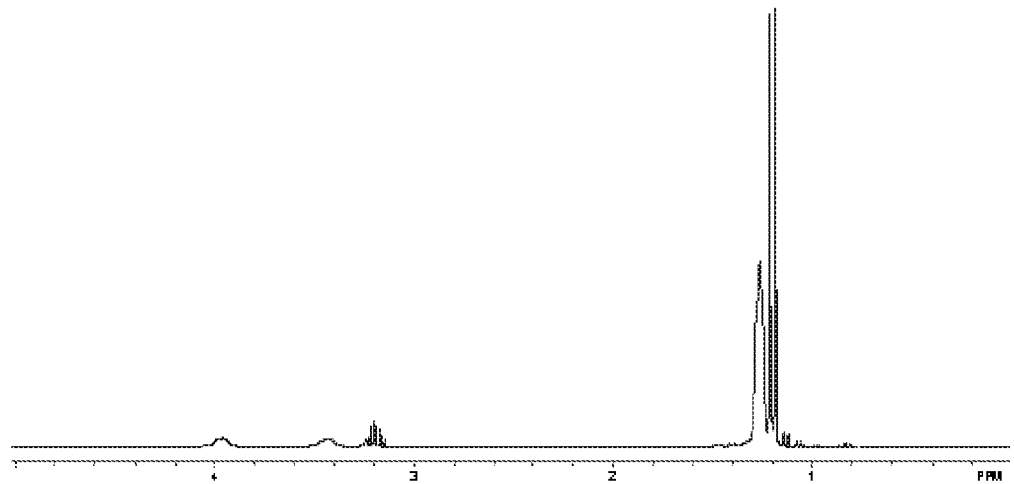
FIG. 1 is an $^1$H-NMR plot for copper (I) 2-isopropyl-1,3-diisopropylamidinate.

The present invention relates to novel copper (I) amidinate precursors for the CVD or ALD formation of copper thin films on substrates, and to corresponding processes for using such precursors.

Amidinates are bulky monoanionic ligands which have the basic chemical structure:

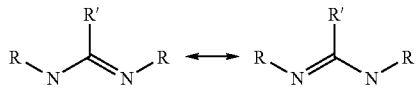

In one aspect, the invention provides a compound of the formula:

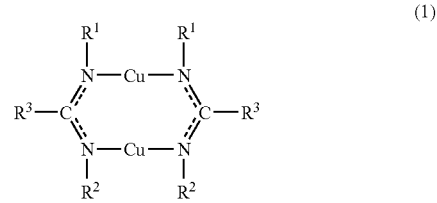

(1)

wherein:

$R^1$ and $R^2$ may be the same as or different from one another and each is independently selected from the group consisting of H, $C_1$-$C_6$ alkyl, $C_3$-$C_7$ cycloalkyl aryl, and hydrocarbyl derivatives of silyl groups (e.g., —$SiR_3$, wherein $R^3$ is independently selected from the group consisting of $C_1$-$C_6$ alkyl);

$R^3$ is selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups;

with the proviso that when $R^1$ and $R^2$ are isopropyl groups, $R^3$ is not a methyl group.

The compounds of formula (1) are usefully employed for forming copper thin films by CVD or ALD processes, utilizing process conditions, including appertaining temperatures, pressures, concentrations, flow rates and CVD techniques, as readily determinable within the skill of the art for a given application.

Preferred compounds of formula (1) include copper (I) 2-isopropyl-1,3-diisopropylamidinate:

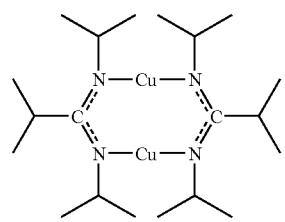

and copper (1) 2-dimethylamino-1,3-diisopropylamidinate:

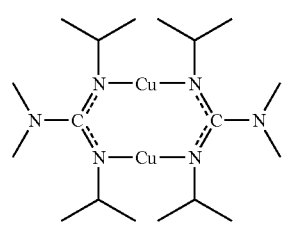

Compounds of formula (1) are readily synthesized according to the following equations (2) and (3):

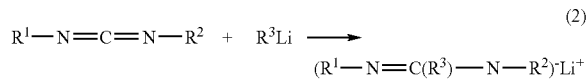

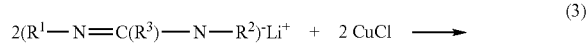

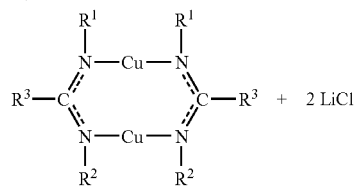

as hereinafter more fully described in the examples herein.

In CVD or ALD usage, the copper (I) precursors of the invention are volatilized to form a precursor vapor that is then contacted with a substrate under elevated temperature vapor decomposition conditions to deposit copper on the substrate.

Copper (I) 2-isopropyl-1,3-diisopropylamidinate and copper (I) 2-dimethylamino-1,3-diisopropylamidinate are both volatile and thermally stable, and are usefully employed as copper CVD or ALD precursors under reducing ambient deposition conditions in the CVD or ALD reactor. The solid precursor can be dissolved in organic solvents, and liquid delivery can be used to meter the solution into a vaporizer for transport to the reactor.

More specifically, and by way of example, the copper (I) amidinate precursor compositions of the present invention may be used during the formation of copper interconnect lines in semiconductor integrated circuitry, thin-film circuitry, thin-film packaging components and thin-film recording head coils. To form such integrated circuitry or thin-film circuitry, a semiconductor substrate may be utilized having a number of dielectric and conductive layers (multilayers) formed on and/or within the substrate. The semiconductor substrate may include a bare substrate or any number of constituent layers formed on a bare substrate.

In the broad practice of the present invention, a copper-containing layer may be formed on a semiconductor substrate using the copper (I) amidinate precursor, for use in a first, second, third, or more metallization layer. Such copper layers typically are used in circuit locations requiring low resistivity, high performance and/or high speed circuit paths. As discussed in the background section hereof, a barrier layer may be deposited or otherwise formed on the substrate before a copper layer is formed on a semiconductor substrate.

Using the copper precursor compositions described herein, copper may then be deposited on the wafer using a CVD or ALD system, such systems being well known in the semiconductor fabrication art. Further, water, water-generating compounds, or other adjuvants to the precursor formulation may be mixed with the copper precursor upstream of, or within, the CVD or ALD tool. Similarly, reducing agents may be utilized in an analogous fashion.

As a further variation, when copper alloy compositions are to be deposited on the substrate, the copper precursor formulation may contain or be mixed with other metal source reagent materials, or such other reagent materials may be separately vaporized and introduced to the deposition chamber.

The compositions of the present invention may be delivered to a CVD or ALD reactor in a variety of ways. For example, a liquid delivery system may be utilized. Alternatively, a combined liquid delivery and flash vaporization process unit may be employed, such as the LDS300 liquid delivery and vaporizer unit (commercially available from Advanced Technology Materials, Inc., Danbury, Conn.), to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD or ALD process.

In liquid delivery formulations, copper precursors that are liquids may be used in neat liquid form, or liquid or solid copper precursors may be employed in solvent formulations containing same. Thus, copper precursor formulations of the invention may include solvent component(s) of suitable character as may be desirable and advantageous in a given end use application to form copper on a substrate. Suitable solvents may for example include alkane solvents, e.g., hexane, heptane, octane, pentane, or aryl solvents such as benzene or toluene, amines and amides. The utility of specific solvent compositions for particular copper precursors may be readily empirically determined, to select an appropriate single component or multiple component solvent medium for the liquid delivery vaporization and transport of the specific copper precursor employed.

In another embodiment of the invention, a solid delivery system may be utilized, for example, using the ProE-Vap solid delivery and vaporizer unit (commercially available from Advanced Technology Materials, Inc., Danbury, Conn.).

A wide variety of CVD or ALD process conditions may be utilized with the precursor compositions of the present invention. Generalized process conditions may include substrate temperature ranges of 150-400° C.; pressure ranges of 0.05-5 Torr; and carrier gas flows of helium, hydrogen, nitrogen, or argon at 25-750 sccm at a temperature approximately the same as the vaporizer of 50 to 120° C.

The deposition of copper thin films with useful electrical properties (low resistivity) and good adhesion to the barrier layer (e.g., formed of TiN or TaN), are also achieved by the process and precursors of the present invention. The conformality of the deposited film is practically achievable through CVD or ALD techniques that preferably provide a pathway to the achievement of "full-fill" copper metallization. The liquid delivery approach of the present invention, including "flash" vaporization and the use of copper precursor chemistry as herein disclosed, enable next-generation device geometries and dimensions to be attained, e.g., a conformal vertical interconnect of 65 nanometer linewidths. The conformal deposition of interconnects of these critical dimensions cannot be realized by currently available physical deposition methods. Thus, the approach of the present invention affords a viable pathway to future generation devices, and embodies a substantial advance in the art.

The features and advantages of the invention are more fully shown by the following illustrative and non-limiting examples.

EXAMPLE 1

Synthesis of Copper (I) 2-isopropyl-1,3-diisopropylamidinate

The reaction was carried out under a steady flow of nitrogen. A Schlenk flask was charged with 6.3 g of 1,3-diisopropylcarbodiimide ($(CH_3)_2CHN=C=NCH(CH_3)$, 49.9 mmol) and 50 mL dry ether and placed in an ice bath. Then, 32 mL of isopropyllithium (1.6M in ether, 51.2 mmol) was added dropwise to the magnetically stirred mixture at about 0° C. After the addition was complete, the mixture was stirred at room temperature for two additional hours. The mixture was transferred to another flask containing 6 g of CuCl (60.6 mmol) suspended in 50 mL ether. This mixture was stirred at room temperature overnight and then stripped to dryness. The solid residue was extracted with pentane (3×50 mL). After extraction, the pentane filtrate was concentrated to slightly cloudy. The saturated solution was placed in a freezer at −39° C., and crystalline product was obtained in a yield of about 60%.

FIG. 1 shows the $^1$H NMR ($C_6D_6$) for copper (I) 2-isopropyl-1,3-diisopropylamidinate, having the following peaks: δ 1.20 (d, 6H, $(CH_3)_2CH$—C), 1.23 (br, 12H, $(CH_3)_2$ CH—N), 3.20 (hept, 1H, CH), 3.45 (br, 1H, CH), 3.95 (br, 1H, CH).

Figure 2:
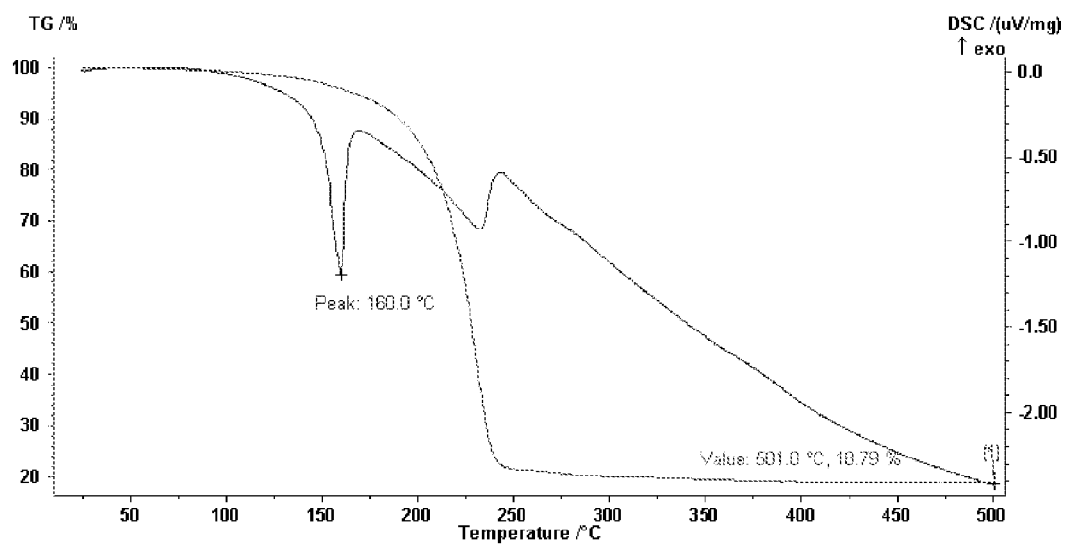
FIG. 2 is a simultaneous thermal analysis (STA)/differential scanning calorimetry (DSC) plot for copper (I) 2-isopropyl-1,3-diisopropylamidinate.

FIG. 2 shows the STA/DSC plot for copper (I) 2-isopropyl-1,3-diisopropylamidinate. The melting peak is about 160° C. and the residue is about 19%.

Figure 3:
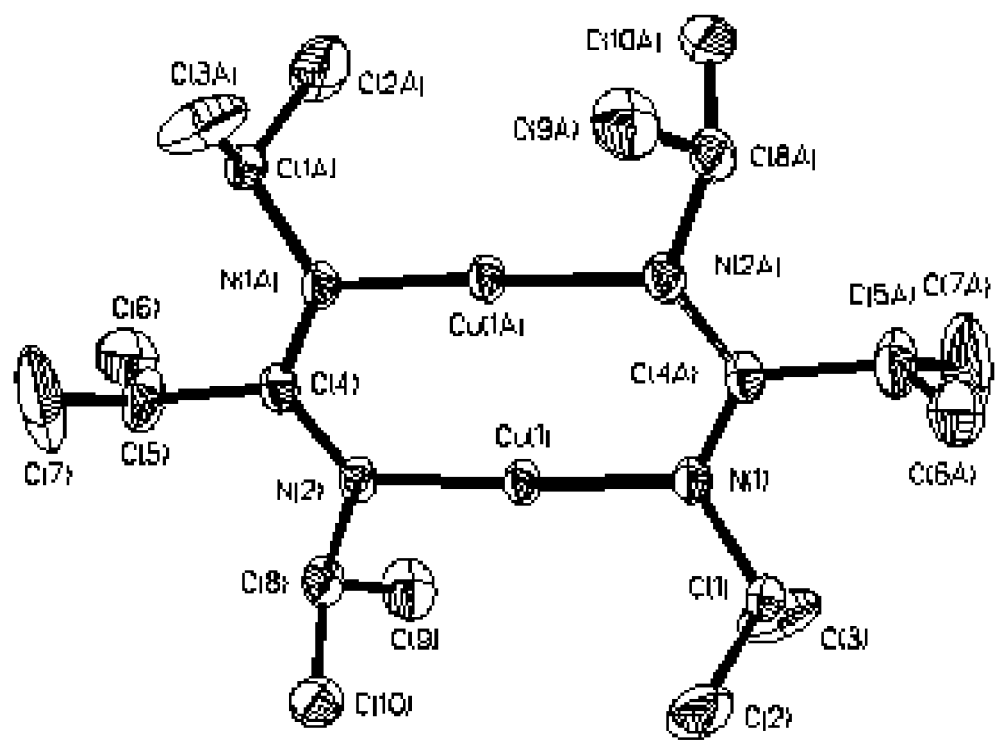
FIG. 3 is an ORTEP structure for copper (I) 2-isopropyl-1,3-diisopropylamidinate.

FIG. 3 is the ORTEP structure for copper (I) 2-isopropyl-1,3-diisopropylamidinate, showing the dimeric structure of the compound and 30% probability thermal ellipsoids.

EXAMPLE 2

Synthesis of Copper (I)
2-dimethylamino-1,3-diisopropylamidinate

Neat 1,3-diisopropylcarbodiimide (12.37 g, 98 mmol, 15.2 mL) was slowly added to a solution of $LiNMe_2$ (5 g, 98 mmol) in 125 mL of THF. Some heat generation was observed. The reaction mixture was stirred for 1 hour. Thereafter, 9.7 g of solid CuCl (98 mmol) was added to the reaction mixture in a dry box. The resulting greenish suspension was stirred overnight and all volatiles were removed in vacuum. The residue was washed in 150 mL of hexane. Filtrate was concentrated in vacuum and placed in a refrigerator whereby neat crystals grew overnight. The overall yield was 60% and the melting point of the crystals was 108° C. $^1$H NMR ($C_6D_6$): δ 3.42 (septet, 1H, J(H—H)=6 Hz, $CH(CH_3)_2$), 2.55 (singlet, 3H, $N(CH_3)_2$), 1.30 (doublet, 6H, J(H—H)=6 Hz, $CH(CH_3)_2$). $^{13}$C NMR ($C_6D_6$): δ 171.95 ($Me_2NC(N(iPr))_2$), 48.61 ($CH(CH_3)_2$), 41.29 ($N(CH_3)_2$), 27.98 ($CH(CH_3)_2$)

Figure 4:
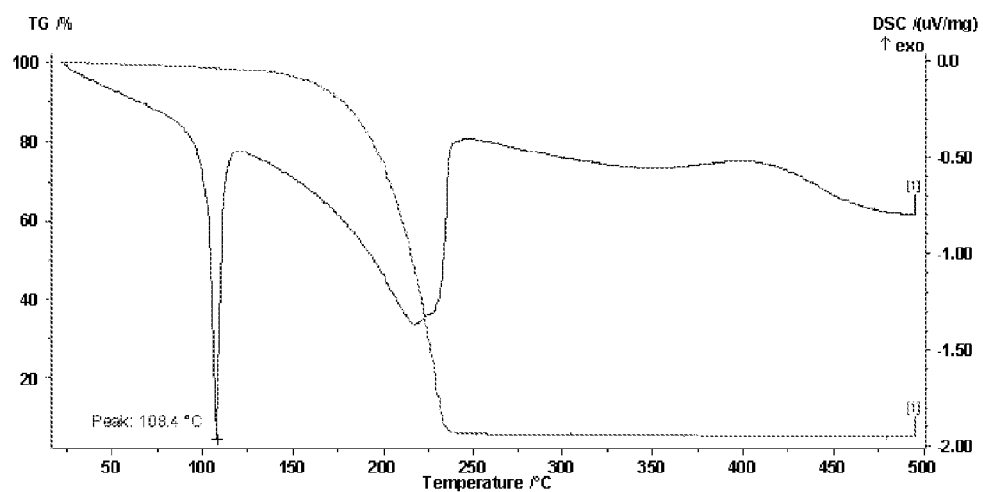
FIG. 4 is an STA/DSC plot for copper (I) 2-dimethylamino-1,3-diisopropylamidinate.

FIG. 4 shows the STA/DSC plot for copper (I) 2-dimethylamino-1,3-diisopropylamidinate, which is volatile with the transport temperature below 230° C., and having a residual mass below 5%.

Figure 5:
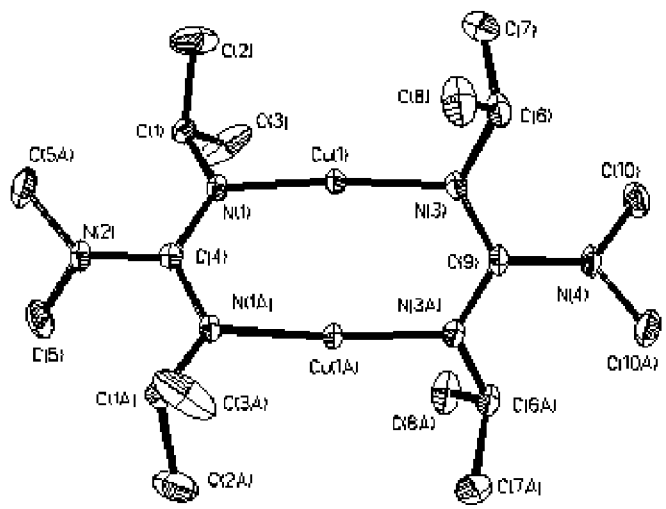
FIG. 5 is an ORTEP structure for copper (I) 2-dimethylamino-1,3-diisopropylamidinate.

FIG. 5 is the ORTEP structure for copper (I) 2-dimethylamino-1,3-diisopropylamidinate, showing the dimeric structure of the compound in the solid state. A relatively short Cu—Cu distance of 2.4152(17) Å may indicate a weak metal-metal interaction. The average Cu—N distance is 1.875(3) Å, which is quite similar to that observed in analogous compounds.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A method of depositing copper on a tantalum or tantalum-containing layer, said method comprising forming a vapor of a copper precursor of the formula:

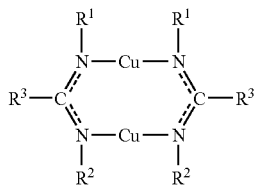

wherein:
R$^1$ and R$^2$ may be the same as or different from one another and each is independently selected from the group consisting of H, $C_1$-$C_6$ alkyl, $C_3$-$C_7$ cycloalkyl, aryl, and hydrocarbyl derivatives of silyl groups;
R$^3$ is selected from the group consisting of H, $C_1$-$C_6$ alkyl, $C_3$-$C_7$ cycloalkyl, aryl, hydrocarbyl derivatives of silyl groups and NR$^4$R$^5$, where R$^4$ and R$^5$ may be the same as or different from one another and is independently selected from the group consisting of H, $C_1$-$C_6$ alkyl, $C_3$-$C_7$ cycloalkyl, aryl, and hydrocarbyl derivatives of silyl groups; and
contacting the copper precursor vapor with the tantalum or tantalum-containing layer to deposit copper on said layer.

2. The method of claim 1, wherein said copper precursor vapor is at temperature in a range of from 50° C. to 120° C.

3. The method of claim 2, wherein said tantalum or tantalum-containing layer is at. temperature in a range of from 150° C. to 400° C.

4. The method of claim 2, wherein the copper precursor vapor is at a pressure in a range of from 0.05 to 5 torr.

5. The method of claim 2, wherein the copper precursor vapor is carried to the tantalum or tantalum-containing layer in a carrier gas for said contacting.

6. The method of claim 5, wherein the carrier gas has a flow rate of from 25 to 750 standard cubic centimeters per minute.

7. The method of claim 6, wherein the carrier gas comprises at least one gas selected from the group consisting of helium, hydrogen, nitrogen and argon.

8. The method of claim 1, wherein said forming the copper precursor vapor comprises liquid delivery flash vaporization of the copper precursor.

9. The method of claim 8, wherein said liquid delivery flash vaporization comprises delivery of said copper precursor in a liquid medium comprising at least one solvent.

10. The method of claim 9, wherein the liquid medium comprises a solvent selected from the group consisting of hexane, heptane, octane, pentane, beuzene, toluene, and dimethylformamide.

11. The method of claim 1, wherein the copper precursor is selected from the group consisting of copper (I) 2-isopropyl-1,3-diisopropylamidinate and copper (I) 2-dimethy-lamine-1,3-diisopropylamidinate.

12. The method of claim 11, wherein the copper precursor is copper (I) 2-dimethylamine-1 ,3-diisopropylamidinate.

13. The method of claim 1, wherein: said copper precursor vapor is at temperature in a range of from 50° C. to 120° C.; said tantalum or tantalum-containing layer is at temperature in a range of from 150° C. to 400° C.; the copper precursor is selected from the group consisting of copper (I) 2-isopropyl-1,3-diisopropylamidmate and copper (I) 2-dimethylamine-1,3-diisopropylamidinate; the copper precursor vapor is at a pressure in a range of from 0.05 to 5 torr; said forming the copper precursor vapor comprises liquid delivery flash vaporization of the copper precursor; and the liquid in said liquid delivery flash vaporization comprises a solvent selected from the group consisting of alkanes, aryls, amines, amides, hexane, heptane, octane, pentane, benzene, toluene, and dimethylformamide.

14. The method of claim 13, wherein said contacting comprises chemical vapor deposition or atomic layer deposition.

15. A precursor vapor comprising vapor of a copper precursor of the formula:

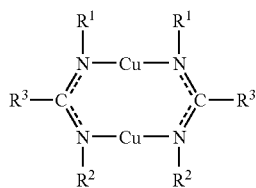

wherein:
$R^1$ and $R^2$ may be the sane as or different from one another and each is independently selected from the group consisting of H, $C_1$-$C_6$ alkyl, $C_3$-$C_7$ cycloalkyl, aryl, and hydrocarbyl derivatives of silyl groups;
$R^3$ is selected from the group. consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups; and
water vapor or vapor of a water-generating compound.

16. The precursor vapor of claim 15, comprising vapor of a copper precursor selected from the group consisting of copper (I) 2-isopropyl-1,3-diisopropylaxnidinate and copper (I) 2-dimethylamine-1,3-diisopropylarnidinate.

17. A solid delivery and vaporizer system for supplying copper precursor vapor for vapor deposition of copper, said system comprising a vessel containing said copper precursor and adapted for delivery from the vessel of copper precursor vapor deriving from the solid copper precursor in the vessel, said solid copper precursor comprising a copper precursor of the formula

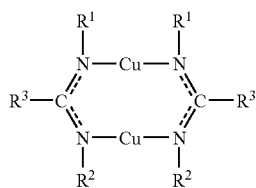

wherein:
$R^1$ and $R^2$ may be the same as or different from one another and each is independently selected from the group consisting of H, $C_1$-$C_6$ alkyl, $C_3$-$C_7$ cycloalkyl, aryl, and hydrocarbyl derivatives of silyl groups;
$R^3$ is selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and is independently selected from the group consisting of H, $C_1$-$C_6$ alkyl, $C_3$-$C_7$ cycloalkyl, aryl, and hydrocarbyl derivatives of silyl groups.

18. The solid delivery and vaporizer system of claim 17, wherein the copper precursor is selected from the group consisting of copper (I) 2-isopropyl-1,3-dilsopropylamidinate and copper (I) 2-dimethylamine-1,3-diisopropylamidinate.

19. The solid delivery and vaporizer system of claim 17, wherein the copper precursor comprises copper (I) 2-dimethylamine-1,3-diisopropylaxnidinate.

20. The method of claim 1, wherein the contacting comprises copper metallization utilizing liquid delivery flash vaporization of the copper precursor and chemical vapor deposition or atomic layer deposition.

21. A copper precursor compound of the formula:

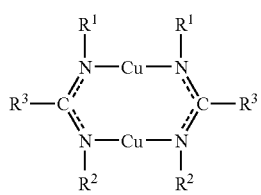

Wherein:
$R^1$ and $R^2$ may be the same as or different from one another and each is independently selected from H and $C_3$-$C_7$ cycloalkyl, and each $R^3$ may be the same as or different from the other, and is independently selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups.

22. A copper precursor compound of the formula:

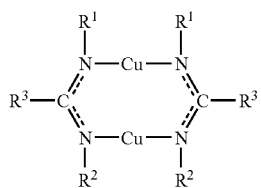

wherein:
each of $R^1$ and $R^2$ may be the same as or different from the others and each is independently selected from the group consisting of H, $C_1$-$C_6$ alkyl, $C_3$-$C_7$ cycloalkyl, and hydrocarbyl derivatives of silyl groups; and
each $R^3$ may be the same as or different from the other and each is independently selected from the group consisting of $C_3$-$C_7$ cycloalkyl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, and hydrocarbyl derivatives of silyl groups;
with the proviso that when $R^1$ and $R^2$ are isopropyl groups, $R^3$ is not a methyl group, and with the proviso that when $R^3$ is H, $R^1$ and $R^2$ ≠propyl or butyl.

23. A solid delivery system for use in depositing copper, said system comprising a solid delivery and vaporizer unit, and a solid delivery copper source material in said solid delivery and vaporizer unit, said copper source material comprising a compound selected from the group consisting of:

(a) compounds of the formula

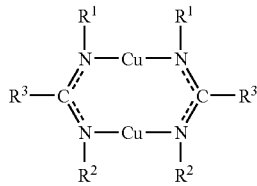

wherein:
each of $R^1$ and $R^2$ may be the same as or different from the others and each is independently selected from the group consisting of H, $C_1$-$C_6$ alkyl, $C_3$-$C_7$ cycloalkyl, aryl, and hydrocarbyl derivatives of silyl groups;
each $R^3$ may be the same as or different from the other and each is independently selected from the group consisting of H, $C_1$-$C_6$ alkyl, $C_3$-$C_7$ cycloalkyl, aryl, hydrocarbyl derivatives of silyl groups and $NR^4R^5$, where R4 and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups;

(b) compounds of the formula

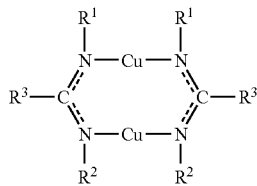

wherein:
each of $R^1$ and $R^2$ may be the same as or different from the others and each is independently selected from H and $C_3$-$C_7$ cycloalkyl, and each $R^3$ may be the same as or different from the other and each is independently selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups; and (c) compounds of the formula

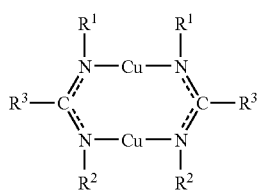

wherein:
each of $R^1$ and $R^2$ may be the same as or different from the others and each is independently selected from the group consisting of H, $C_1$-$C_6$ alkyl, $C_3$-$C_7$ cycloalkyl, aryl, and hydrocarbyl derivatives of silyl groups;
each $R^3$ may be the same as or different from the others and each is independently selected from the group consisting of $C_3$-$C_7$ cycloalkyl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups;
with the proviso that when $R^1$ and $R^2$ are isopropyl groups, $R^3$ is not a methyl group.

24. A solid delivery process for depositing copper, said process comprising vaporizing a solid source material to generate a copper precursor vapor, and depositing copper from said copper precursor vapor on a substrate, wherein said copper precursor vapor comprises vapor of a copper precursor selected from the group consisting of:

(a) compounds of the formula

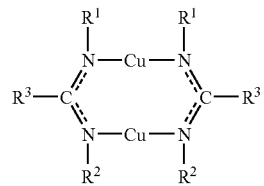

wherein:
each of $R^1$ and $R^2$ may be the same as or different from the others and each is independently selected from the group consisting of H, $C_1$-$C_6$ alkyl, $C_3$-$C_7$ cycloalkyl, aryl, and hydrocai-byl derivatives of silyl groups;
each $R^3$ may he the same as or different from the other and each is independently selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups;

(b) compounds of the formula

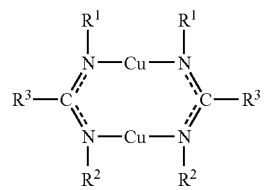

wherein:
each of $R^1$ and $R^2$ may be the same as or different from the others and each is independently selected from H and $C_3$-$C_7$ cycloalkyl, and each $R^3$ may be the same as or different from the other and each is independently selected from the group consisting of H, $C_1$-$C_6$ alkyl, $C_3$-$C_7$ cycloalkyl, aryl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups; and (c) compounds of the formula

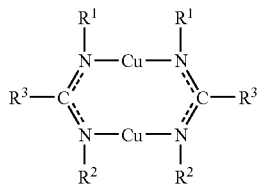

wherein:

each of $R^1$ and $R^2$ may be the same as or different from the others and each is independently selected from the group consisting of H, $C_1$-$C_6$ alkyl, $C_3$-$C_7$ cycloalkyl, aryl, and hydrocarbyl derivatives of silyl groups;

each $R^3$ may be the same as or different from the others and each is independently selected from the group consisting of $C_3$-$C_7$ cycloalkyl, hydrocarbyl derivatives of silyl groups and $NR^4R^5$, where $R^4$ and $R^5$ may be the same as or different from one another and each is independently selected from the group consisting of H, $C_1$-$C_6$ alkyl, $C_3$-$C_7$ cycloalkyl, aryl, and hydrocarbyl derivatives of silyl groups; with the proviso that when $R^1$ and $R^2$ are isopropyl groups, $R^3$ is not a methyl group.

25. A composition comprising copper (I) 2-isopropyl-1,3-diisopropylamidinate in an organic solvent medium.

26. The composition of claim 25, wherein said solvent medium comprises toluene.

27. A composition comprising copper (I) 2-dimethylamine-1,3-diisopropylamidinate in an organic solyent medium.

28. The composition of claim 27, wherein said solvent medium comprises toluene.

29. A copper precursor compound of the formula:

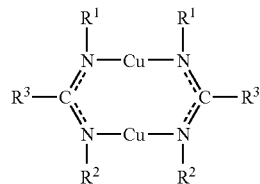

wherein:

$R^1$ and $R^2$ may be the same as or different from one another and each is independently selected from $C_1$-$C_6$ alkyl; $R^3$ is $NR^4R^5$, where $R^4$ and $R^5$ may be the same as or different from one another and is independently selected from $C_1$-$C_6$ alkyl.

30. The method of claim 9, wherein said at least one solvent is selected from the group consisting of alkane, aryl, amine and amide solvents.

31. The method of claim 20, wherein said copper metallization comprises full fill copper metallization.

* * * * *